United States Patent [19]

Sonoyama et al.

[11] 4,287,137

[45] Sep. 1, 1981

[54] VANE-TYPE FLUID IMPELLER AND METHOD OF AERATING A LIQUID

[75] Inventors: Takayasu Sonoyama, Sakai; Hiroyoshi Tani, Ibaraki; Kobee Kobayashi, Takatsuki, all of Japan

[73] Assignee: Shionogi & Co., Ltd., Osaka, Japan

[21] Appl. No.: 110,444

[22] Filed: Jan. 8, 1980

[30] Foreign Application Priority Data

Jan. 8, 1979 [JP] Japan .................. 54-5103

[51] Int. Cl.³ .............................................. B01F 3/04
[52] U.S. Cl. .................................... 261/93; 209/169; 210/220; 416/189; 435/315
[58] Field of Search .............................. 261/87, 91, 93; 435/312, 313, 315; 209/169, 170; 210/219, 220, 221 P; 416/179, 181, 189, 191 R

[56] References Cited

U.S. PATENT DOCUMENTS

| | | | |
|---|---|---|---|
| 53,504 | 3/1866 | Thompson | 261/93 X |
| 687,182 | 11/1901 | Franklin | 416/189 |
| 933,090 | 9/1909 | Mason et al. | 261/87 |
| 1,135,451 | 4/1915 | Heath | 416/189 |
| 1,417,883 | 5/1922 | Beers | 261/87 X |
| 2,320,469 | 6/1943 | Rasmussen | 261/93 X |
| 2,521,396 | 9/1950 | Moul | 261/93 |
| 3,210,179 | 10/1965 | Davis et al. | 435/315 X |
| 3,539,273 | 11/1970 | Arshal | 416/189 X |
| 3,642,257 | 2/1972 | Tanaka et al. | 261/93 |
| 3,680,847 | 8/1972 | Grutsch et al. | 261/91 |

Primary Examiner—Richard L. Chiesa
Attorney, Agent, or Firm—Birch, Stewart, Kolasch and Birch

[57] ABSTRACT

A provision of the disclosed grating composed of closed loops of plurality of parallelly-arranged straps with clearances between adjacent straps is made to encompass a space of a body of a revolution defined by a vane-type impeller. It proves to be effective for improving gas-absorption by a better gas-liquid contact in a chemical process or fermentation process.

22 Claims, 8 Drawing Figures

VANE-TYPE FLUID IMPELLER AND METHOD OF AERATING A LIQUID

BACKGROUND OF THE INVENTION

1. Field of the Invention

The present invention generally relates to the art of chemical or fermentation processes and equipment therefor. More particularly, it is concerned with a vane-type impeller capable of performing a gas-liquid contact which may frequently be required in chemical or fermentation process to improve the efficiency thereof.

Fermentors equipped with impellers and aerating spargers have been customarily used in the field of fermentation industry since the introduction of so-called submerged culture in the production of penicillin.

As well known in the art, uniform dispersion of microorganisms throughout the liquid broth in the fermentor and sufficient supply of substrate to the microorganisms are fundamental requirements in an aerating and agitating operation of the fermentation process.

In the other words, continuous supply of various substrates, e.g., nutrients, oxygen and hydrogen ion into the liquid broth and removal of excreta and exhaust gas of the microorganisms therefrom must be performed under suitable admixing while avoiding undesirable localization of these substrates as well as heat.

Among the constituents of the substrates, oxygen is essential for the growth of most industrially utilizable aerobic microorganisms but it is only sparingly soluble in any aqueous medium.

2. Description of the Prior Art

As is well known, the ability of equipment for supplying the liquid medium with oxygen is dominating the entire progress of the fermentation in ones which requires a vast amount of oxygen, for instance, gluconic acid production from sugars and yeast production utilizing substrate of molasses or normal paraffines. Therefore, a large amount of power consumption for the aeration and agitation of the liquid medium has been considered to be inevitable in conventional equipment.

The cost for the consumed power for aeration and agitation may sometimes occupy over 70% of the entire utility expense. In addition to this, a major proportion of the consumed power has been converted into heat which might frequently be removed with additional expenses.

There has hitherto been known a system equipped with a sparger or a perforated pipe distributor which includes a gas injecting means wherein gas is injected through the axis of rotation of an impeller for the purpose of providing fine bubble distribution in the liquid medium.

The former system employs a sintered metal or ceramic filter as the diffuser solely or combined with a blade-type impeller. The high oxygen diffusing ability of the stated spargers observed with a system of water and an inorganic solute, for instance, sodium sulfate is reduced conspicuously with a fermentation broth whose physical characteristics are utterly different from those of the former system.

In addition to this, no significant reduction in the power consumption is observed with a combination of paddle-type impeller with a perforated pipe distributor as compared with another combination of impeller with a single straight-type nozzle. Moreover, possible clogging of the perforations or interstices between and among the particles of the sintered body with clots of the microorganisms from the fermentation broth might make a lengthy and continuous operation or repeated operations very difficult.

As can be easily seen, the latter system of inletting gas through a rotating axis of an impeller has no distinct advantage over the former in view points of design, operation and maintenance.

An excessive acceleration of liquid flow usually accompanied by mixing operation might damage the miroorganisms in some instances and lead to the generation of useless frictional heat and wasteful consumption of energy resources.

Hence, the advent of an efficient aeration system has been eagerly desired though, a practical one which is satisfactory in and all respects has not yet been proposed to date.

SUMMARY OF THE INVENTION

It is therefore a primary object of the present invention to provide a vane-type fluid impeller capable of performing uniform dispersion of gas into liquid with an improved efficiency.

Another object of the present invention is to provide an impeller capable of reducing the overall cost for building a reactor or fermentor equipped the impeller as well as reducing the power consumption required in such facility.

A further object of the present invention is to provide an impeller capable of reducing the dimension of the obtained gas bubbles, thus improving the dispersion of gas into liquid.

A still other object of the present invention is to provide an impeller capable of maintaining the dimension of the fine bubbles by preventing possible fusion of the once formed bubbles.

A still further object of the present invention is to provide an impeller which obviates undesirable reduction of gas absorption efficiency in using any objectionable agent such as surfactant.

A still other object of the present invention is to provide an impeller of simple structure offering a great freedom in design and construction for fulfilling the stated objects.

A still further object of the present invention is to provide an impeller capable of utilizing oxygen for the process while inhibiting excessive acceleration of the liquid flow which may result in a wasteful conversion of the energy into heat which must be eliminated from the reactor or fermentor with additional expenses.

These and other objects as well as attendant advantages of the present invention will be apparent from the following description.

According to the present invention, there is provided an improvement in a vane-type fluid impeller having an axis of rotation and at least one blade or vane defining a given space of a body of revolution about the axis, and being capable of forcing at least part of a gas-liquid mixture through said space while being rotated.

The improvement is characterized in the provision of grating composed of at least one strap substantially surrounding and co-rotating with said impeller, i.e. closed loop(s) of a plurality of parallelly-arranged straps with clearances between the adjacent straps, substantially encompassing said space; each of said loops defining a plane substantially perpendicular to said axis.

Said grating, the closed loops of strap, may preferably be secured directly onto outer periphery of said impeller, but may be so arranged by any other suitable means, for instance, with independent stems radially planted on a hub around the axis of rotation.

Said blade or vane may be of a single plate spirally would around the hub or may be composed of a plurality of paddles, planted around the hub with or without some axial pitch. Each of them, however, needs to have an ability of forcing at least part of the gas-liquid mixture though the slits of the grating or upon the straps constituting the grating.

Preferably each of said loops may define a plane substantially perpendicular to the axis but may be biased towards said plane, and in such cases the plurality of the loops may be combined with the blade or vane by winding or threading a single strand around the outer periphery of the impeller.

Furthermore, said closed loop may be circular, circumscribed about the outer edges, i.e., distals, of the blade or vane, or may be a polygonal shape inscribed in the circle formed by connecting the outer edges.

The impeller of the present invention having the above described structure is usually installed in a vessel for gas-liquid contact reaction or in a fermenator for aerobic microorganism and in close proximity to a nozzle head which injects gas into the liquid in the vessel or the fermenter.

The injected gas needs to be dispersed uniformly into the liquid as minute bubbles while it is propelled through the space defined by the impeller together with the entrained liquid.

Although a minor portion of the injected gas is forced through the space in the direction of the axis, a major portion thereof is diverted from the space to impinge upon the grating to be sheared to become abundant in finer bubbles.

In another aspect of the present invention, the impeller may have at least one closed loop of strap arranged at the side periphery of the impeller, in addition to the loops on the outer periphery, and in such case the side loop may further be multiplied to be arranged concentrically with the axis or may be of a single strand of strap which is arranged swirlingly or spirally around the center.

This may be done for the purpose of maximizing the shearing and dispersing effect of the impeller in accordance with the shape of the vessel to be installed and the mode of installation. The vessel may be tall or thickset and the impeller may be installed vertically, horizontally or obliquely with respect to the center axis of the vessel.

In this way the once formed fine bubbles are prevented from possible fusion to form coarser bubbles thus making the gas-liquid contact more effective.

Straps of any cross-sectional shape, for instance, circular, elliptic, rectangular or polygonal ones may be employed as the component of the grating so far as the shape holds a shearing ability sufficient for fulfilling the stated purpose.

DESCRIPTION OF THE PREFERRED EMBODIMENTS

Figure 1:
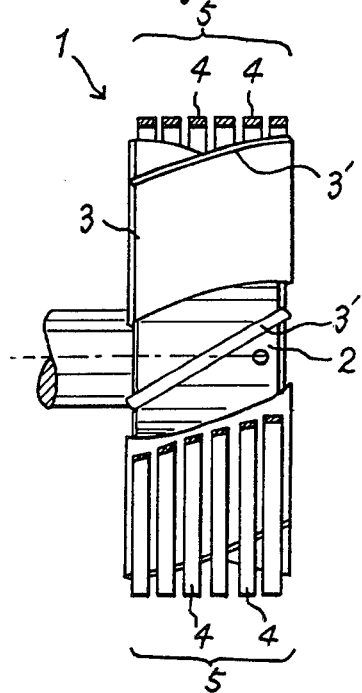
Figure 2:
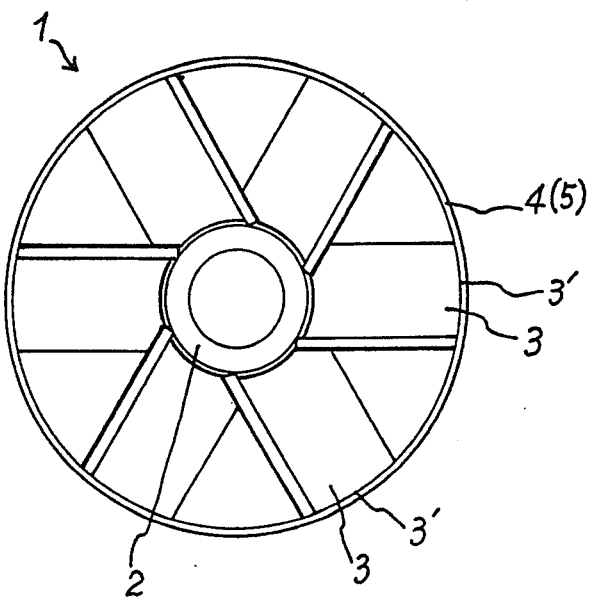
Figure 3:
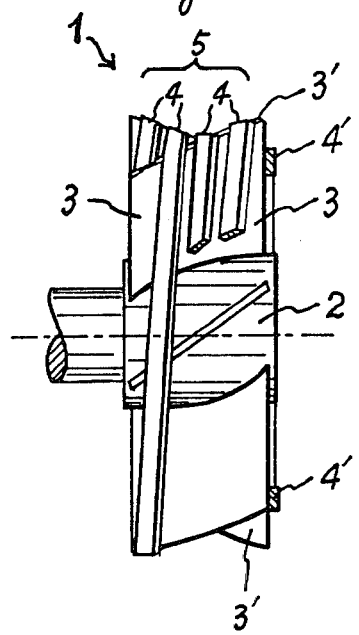
Figure 4:
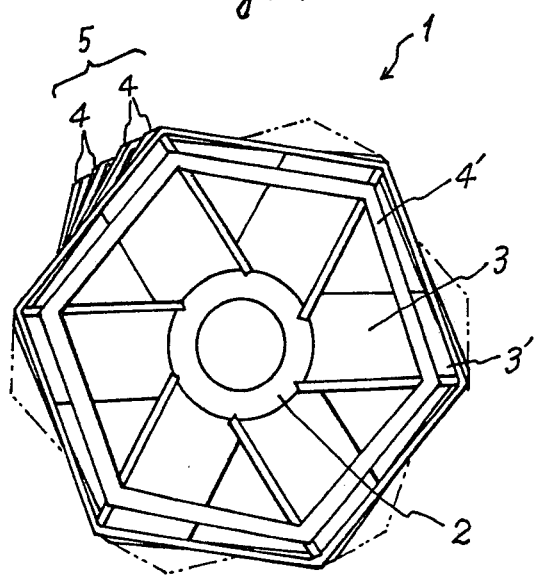
Figure 5:
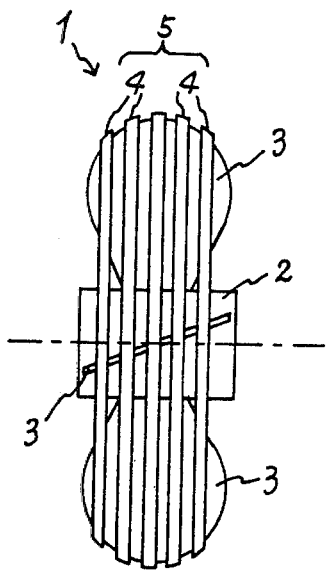
Figure 6:
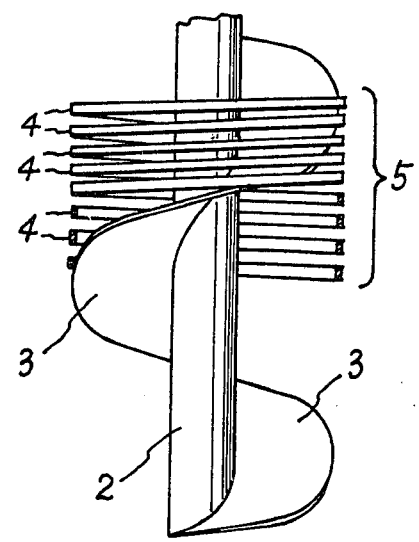
Figure 8:
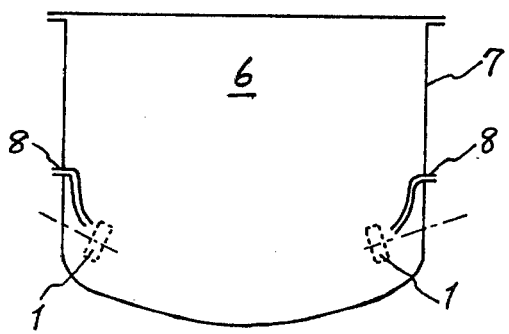
Figure 7:
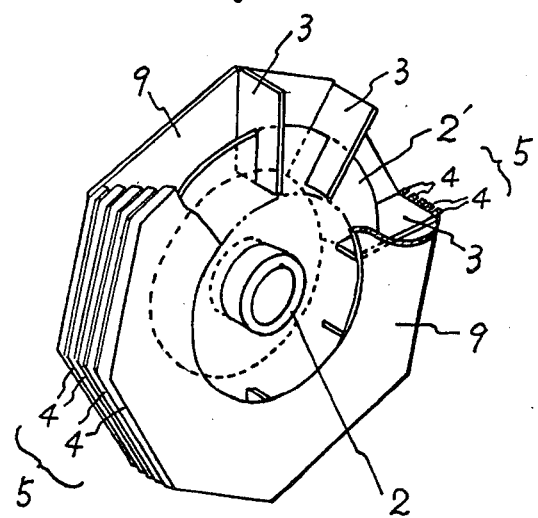

Other objects, features and advantages of the present invention will be more fully understood from the following description of the embodiments thereof taken in conjunction with the accompanying drawings, in which;

FIG. 1 is a side view of an embodiment of the vane-type impeller built in accordance with the present invention, partly broken away for illustration, FIG. 2 is a front view of the embodiment of FIG. 1, FIG. 3 is a side view of another embodiment, partly broken away for illustration, FIG. 4 is a front view of the embodiment of FIG. 3, FIGS. 5 and 6 are side views of additional embodiments, FIG. 7 is a partially broken away perspective view of another embodiment, and FIG. 8 is a schematic cross-section of a fermentor equipped with the impellers of one embodiment, indicating the mode of arrangement of the impellers in the fermentor.

The identical or related reference numerals are used to indicate the corresponding parts or components of the exemplified impellers as well as an apparatus equipped with the impeller, throughout several views. In each of the figures, numeral 1 indicates inclusively an impeller which has a center hub 2, vane(s) or blade(s) 3 radially planted on the hub 2, and a grating 5 composed of a plurality of closed loops of strand 4 encompassing the outer periphery of the body of revolution defined by the vane(s). The grating 5 is usually secured to distal(s) 3' of the blade(s) by rivetting or welding, though it may alternatively be supported by independent stems (not shown) planted directly on the hub 2.

In the embodiments of FIGS. 3, 4 and 6, the strand 4 is wound spirally around the impeller 1 to form the grating 5. A side loop 4' is also provided on the front face of the impeller 1 of the former embodiments. Only part of the strand 4 wound around a single spiral vane 3 is shown in FIG. 6. In FIG. 7, vanes 3 without any axial pitch are supported by a disk 2' attached to the hub 2 and by both side plates 9.

As can be seen from FIG. 8, the impellers 1 are arranged in front of the outlets or nozzles 8 for gas along waistline of a side wall 7 of a container, fermentor or reactor 6.

The previously described advantages of the impeller of the present invention will be discussed in further detail by referring to the following experimental results.

EXPERIMENT 1

A cylindrical fermenter having an internal diameter of 1,200 mm and an effective fluid capacity of 600 l is equipped with three impellers of the type illustrated in FIG. 3 of diameter of 120 mm and depth of 31 mm.

The impellers are arranged equally spaced-apart along the waistline of the inner wall of the fermenter and directed obliquely downwards toward the center of the fermenter as illustrated in FIG. 8.

Aeration of a broth (600 l) including baker's yeast placed in the fermenter is performed at a rate of 200 Nl/min to obtain an apparent oxygen absorbing capacity coefficient K'd (a value calculated based on an oxygen absorbing rate of the baker's yeast at its steady state) as stated below.

A value obtained with a comparative experiment which employs a conventional pitched paddle (pitch ratio $= \pi$, ratio of blade width to diameter $= 0.3$) is parallelly presented.

| Impeller | Diameter (mm) | Revolution (r.p.m.) | Power consumed (Kw.) | K'd (mole O$_2$ / m$^3$ · hr. · atm) |
|---|---|---|---|---|
| Invention | 120 | 1,300 | 1.61 | 525 |
| Pitched paddle | 250 | 600 | 2.13 | 468 |

EXPERIMENT 2

The identical equipments and similar conditions as employed in Experiment 1 together with those in the comparative experiment are employed.

Degrees of thorough mixing are confirmed with a mixture of water (600 l) and 30% saline water (2.4 l) by measuring the time required for attaining 99% equilibrium to obtain the following results.

| Impeller | Impeller Diameter (mm) | Revolution (r.p.m.) | Power consumed (Kw.) | Time required (sec) |
|---|---|---|---|---|
| invention | 120 | 1,300 | 1.61 | 10 |
| Pitched paddle | 250 | 600 | 2.13 | 22 |

EXPERIMENT 3

K'd value at an aerobic fermentation (15.3 Nl/min) of a broth of baker's yeast (55.8 l) placed in a cylindrical vessel having internal diameter of 474 mm and an effective fluid capacity of 55.8 l, equipped with an impeller of the type illustrated in FIG. 3 (diameter, 72 mm, depth, 18.6 mm) and with an aerating nozzle is compared with a value obtained with an experiment performed in the same vessel except for the provision of a conventional pitched paddle (pitch ratio = $\pi$, ratio of blade width to diameter = 0.3), as summarized below,

| Impeller | Diameter (mm) | Revolution (r.p.m.) | Power consumed (W) | K'd (mole O$_2$ / m$^3$ · hr. · atm) |
|---|---|---|---|---|
| Invention | 72 | 1,300 | 33 | 127 |
| Pitched paddle | 72 | 1,600 | 37.5 | 102 |

What is claimed is:

1. A vane-type fluid impeller for aerating a fluid by injecting a gaseous fluid therein, said gaseous fluid having gas bubbles disposed therein, comprising:
    hub means having an axis of rotation, said gaseous fluid initially moving approximately parallel to said axis of rotation;
    vane means connected with and arranged circumferentially around said hub means for receiving said gaseous fluid and for forcing at least a portion of said gaseous fluid to move approximately perpendicular to the axis of rotation of said hub means; and
    strap means defining a grating substantially surrounding and co-rotating with said vane means for receiving said gaseous fluid from said vane means and for shearing said gas bubbles disposed within said gaseous fluid.

2. An impeller as claimed in claim 1, wherein said grating is secured onto the outer periphery of said vane means and shears the gas bubbles within said gaseous fluid passing therethrough.

3. An impeller as claimed in claim 1, wherein said grating is supported by independent stem means radially secured to said hub means of the impeller with respect to said axis of rotation.

4. An impeller as claimed in claim 1, wherein said vane means includes a plurality of fragmentary elements disposed about said hub means, each of said elements propelling at least part of the gaseous fluid in a direction substantially perpendicular to the axis of rotation of said hub means, said fluid impinging upon said grating, said grating shearing the gas bubbles disposed within said gaseous fluid.

5. An impeller as claimed in claim 1, wherein a plane formed containing said strap means is arranged substantially perpendicular to said axis of rotation.

6. An impeller as claimed in claim 5, wherein a single strand of said strap means is arranged spirally around the outer periphery of said impeller.

7. An impeller as claimed in claim 1, wherein said strap forms a circle or circles circumscribed about the outer periphery of said vane means.

8. An impeller as claimed in claim 1, wherein said strap means forms a polygon connecting the outer edges of said vane means.

9. An impeller as claimed in claim 1, wherein at least one loop of said strap means is formed on the outer periphery of said vane means.

10. An impeller as claimed in claim 9, wherein a plurality of loops of said strap means are arranged coaxially with said axis of rotation.

11. An impeller as claimed in claim 9, wherein a single strand of said strap means is wound spirally about said axis of rotation.

12. An impeller as claimed in claim 1, wherein said strap has a rectangular cross section.

13. An impeller as claimed in claim 1, wherein said strap has a circular cross-section.

14. An impeller as claimed in claim 1, wherein said strap means has a polygonal cross-section.

15. An impeller as claimed in claim 1, wherein said vane means includes a plate spirally wound around said hub means.

16. An impeller as claimed in claim 1, wherein said vane means is arranged with axial pitch.

17. A vane-type fluid impeller in accordance with claim 1, wherein said vane means comprises a plurality of paddles approximately equally spaced around the outer periphery of said hub means, one end of each of said paddles being connected to an outer periphery of said hub means, said paddles being oriented relative to said hub means to receive said gaseous fluid moving approximately parallel to the axis of rotation of said hub means and to force at least a portion of said gaseous fluid to move approximately perpendicular to the axis of rotation of said hub means toward said strap means.

18. A vane-type fluid impeller in accordance with claim 17, wherein each of said plurality of paddles is disposed at a predetermined axial pitch relative to the axis of rotation of said hub means.

19. A vane-type fluid impeller in accordance with claim 17 or 20 wherein said strap means comprises a plurality of loops, an internal surface of each of said loops being in contact with the other end of each of said paddles, each of said loops being disposed closely together and forming a plurality of spaces therebetween for defining said grating, said grating receiving said gaseous fluid moving approximately perpendicular to the axis of rotation and shearing said gas bubbles disposed within said gaseous fluid.

20. A vane-type fluid impeller in accordance with claim 19, wherein each of said loops lie within a plane, said plane being substantially perpendicular to the axis of rotation of said hub means.

21. A gas-liquid contact apparatus for aerating a liquid by injecting a gaseous fluid therein, said gaseous fluid having gas bubbles disposed therein, comprising:
   (a) container means for containing said liquid;
   (b) a vane-type fluid impeller means comprising hub means having an axis of rotation, said gaseous fluid initially moving substantially parallel to said axis of rotation, vane means connected with and arranged circumferentially about said hub means, said vane means forcing at least a portion of said gaseous fluid to move substantially perpendicular to said axis of rotation, and strap means defining a grating substantially surrounding and co-rotating with said vane means for receiving said gaseous fluid and for shearing said gas bubbles disposed within said gaseous fluid; and
   (c) nozzle means arranged in close proximity to said fluid impeller for injecting gas into said liquid thereby forming said gaseous fluid.

22. A chemical or fermentation process wherein a gas is contacted with a liquid to assist said process, comprising the steps of:
   (a) introducing a gas into said liquid thereby forming a gaseous fluid having gas bubbles disposed therein; and
   (b) rotating a vane-type fluid impeller in said gaseous fluid, said impeller comprising,
      (1) hub means having an axis of rotation,
      (2) vane means connected with and arranged circumferentially about said hub means, and
      (3) strap means defining a grating substantially surrounding and co-rotating with said vane means;
   (c) directing said gaseous fluid into said liquid in close proximity to said fluid impeller and to initially move substantially parallel to said axis of rotation, rotating said vane means to receive said gaseous fluid and to direct said fluid toward said strap means; and
   (d) shearing said gas bubbles disposed within said gaseous fluid by means of said strap means.

* * * * *